United States Patent [19]

Kelm et al.

US005785951A

[11] Patent Number: 5,785,951
[45] Date of Patent: Jul. 28, 1998

[54] USE OF KETOROLAC FOR TREATMENT OF ORAL DISEASES AND CONDITIONS

[75] Inventors: Gary Robert Kelm; Harvey Marvin Pickrum; Matthew Joseph Doyle; William Buchanan, all of Cincinnati, Ohio

[73] Assignee: The Procter & Gamble Company, Cincinnati, Ohio

[21] Appl. No.: 503,575

[22] Filed: Jul. 18, 1995

Related U.S. Application Data

[62] Division of Ser. No. 280,163, Jul. 25, 1994, Pat. No. 5,464,609, which is a continuation of Ser. No. 132,426, Oct. 5, 1993, abandoned, which is a continuation of Ser. No. 947,193, Sep. 18, 1992, abandoned, which is a continuation-in-part of Ser. No. 930,493, Aug. 14, 1992, abandoned, which is a continuation of Ser. No. 651,061, Feb. 8, 1991, abandoned, which is a continuation-in-part of Ser. No. 494,697, Mar. 16, 1990, abandoned.

[51] Int. Cl.$^6$ .................... A61K 7/16; A61K 7/22
[52] U.S. Cl. ........................ 424/49; 424/54
[58] Field of Search ............................ 424/49–58

[56] References Cited

U.S. PATENT DOCUMENTS

| | | | |
|---|---|---|---|
| 4,089,969 | 5/1978 | Muchowski et al. | 424/274 |
| 4,578,390 | 3/1986 | Jensen et al. | 514/255 |
| 4,780,320 | 10/1988 | Baker | 424/493 |
| 4,873,430 | 10/1989 | Muchowski et al. | 548/453 |
| 4,874,871 | 10/1989 | Fleming et al. | 548/543 |
| 4,919,939 | 4/1990 | Baker | 424/493 |
| 4,933,172 | 6/1990 | Clark et al. | 424/49 |
| 4,965,262 | 10/1990 | Kametaka et al. | 514/230.2 |

FOREIGN PATENT DOCUMENTS

| | | | |
|---|---|---|---|
| 0137668 | 4/1985 | European Pat. Off. | A61K 31/19 |
| 306984 | 3/1989 | European Pat. Off. | A61K 9/06 |
| 363224 | 4/1990 | European Pat. Off. | A61K 7/16 |
| 380367 | 8/1990 | European Pat. Off. | A61K 31/375 |
| 2501548 | 7/1975 | Germany | A61K 5/00 |
| 2629884 | 1/1977 | Germany | A61K 7/16 |
| 3218-308-a | 9/1991 | Japan | A61K 7/16 |
| 1489672 | 10/1977 | United Kingdom | A61K 7/16 |
| 1550139 | 8/1979 | United Kingdom | A61K 5/08 |
| WO 87/06266 | 10/1987 | WIPO | C12P 17/18 |
| WO 89/00421 | 1/1989 | WIPO | A61K 31/19 |
| WO 91/02512 | 3/1991 | WIPO | A61K 7/16 |
| WO 91/13609 | 9/1991 | WIPO | A61K 7/16 |

OTHER PUBLICATIONS

Barshun, C.L., L.S. Olanoff, D.D. Gleason, E.L. Adkins & N.F.H. Ho, "Human Buccal Absorption of Flurbiprofen," Clin. Pharmacol. Ther., vol. 44, No. 2, pp. 225–231 (Aug. 1988).

Caldwell, J., A.J. Hutt & S. Fournel–Gigleux, "The Metabolic Chiral Inversion and Dispositional Enactioselectivity of the 2-Arylpropionic Acids and their Biological Consequences", Biochemical Pharmacology, Vo., 37, No. 1,(1988), pp. 105–114.

Chin, R.C. & Y. Chen, Orthopaedic Research Society Meeting materials from 35th Annual Meeting, p. 119.(Feb. 6–8, 1989).

Elattar, T. M. A., H. S. Lin and D. E. Tira, "The Effect of Non–steroidal Anti–inflammatory Drugs on the Metabolism of $^{14}$C–Arachidonic Acid by Human Gingival Tissue," J. Dent. Res., vol. 62, No. 9, pp.975–979(Sep. 1983).

Feldman, R.S., B. Szeto, H.H. Chauncey & P. Goldhaber, "Non–Steroidal Anti–inflammatory Drugs in the Reduction of Human Aveolar Bone Loss", Journal of Clinical Periodontology, vol. 10, No. 2 pp. 131–136(1983).

Gaffar, A., J. Afflitto, E.J. Coleman, L. Steinberg & D. Fine, "Efficacy of Ibuprofen Rinse in a Subgingival Irrigator on Periodontitis in Primates", Journal of Dental Research, vol. 68 (Spec. Issue), p.970, Abstract No. 830(Mar. 1989).

Gonzalez–Younes, I., J. G. Wagner, D. A. Gaines, J. J. Ferry & J. M. Hageman, "Absorption of Flurbiprofen Through Buccal Mucosa," Journal of Pharmaceutical Sciences, vol., 80, No. 9, pp. 820–823(Sep. 1991).

Heasman, P. A., R.A. Seymour & P.F. Boston, "The Effect of a Topical Non–Steroidal Anti–Inflammatory Drug on the Development of Experimental Gingivitis in Man", Journal of Clinical Periodontology, vol. 16, pp. 353–358(Jul. 1989).

Heasman, P.A., A. Ward, A.W. Barrett, R.A. Seymour & G. Edwards, "Flurbiprofen in Human Crevicular Fluid Analyzed by High–Performance Liquid Chromatography," J. Periodont. Res., vol. 25, pp. 88–92(1990).

Hutt, A.J. & J. Caldwell, "The Metabolic Chiral Inversion of 2–Arylpropionic Acids —A Novel Route with Pharmacological Consequences", Journal of Pharmacy and Pharmacology, vol. 35(1983), pp. 693–704.

Jeffcoat, M. K., R. Page, M. Reddy, R. Cogen, P. Waite, K. Palcanis, R.C. Williams & C. Basch, "Naproxen as an Adjunct in the Treatment of Rapidly Progressive Periodontitis", Journal of Dental Research, vol. 68, Special Issue-(Mar. 1989), Abstract No. 1055, p. 999.

Jeffcoat, M.K., R.C. Williams, M.S. Reddy, R. English & P. Goldhaber, "Flurbiprofen Treatment of Human Periodontitis: Effect on Alveolar Bone Height and Metabolism", Journal of Periodontal Research, vol. 23(1988), pp. 381–385.

Jeffcoat, M.K., R.C. Williams, W.J. Wechter, H.G. Johnson, M.L. Kaplan, J.S. Gandrup & P. Goldhaber, "Flurbiprofen Treatment of Periodontal Disease in Beagles," Journal of Periodontal Research, vol. 21, pp. 624–633(1986).

Johnson, R.H., G.C. Armitage, C. Francisco & R.C. Page, "Assessment of the Efficacy of Nonsteroidal Anti–inflammatory Drug, Naprosyn®, in the Treatment of Gingivitis", J. Periodont.. Res., vol. 25, pp. 230–235(1990).

(List continued on next page.)

Primary Examiner—Shep K. Rose
Attorney, Agent, or Firm—Milton B. Graff, IV; Douglas C. Mohl; Jacobus C. Rasser

[57] ABSTRACT

The present invention relates to methods and compositions for prevention or treatment of bone loss due to periodontal disease, oral osseous surgery, periodontal flap surgery, tooth extraction, dental implants, or scaling and root planing comprising topical administration, to mucosal tissues of the oral cavity, of a composition having from about 0.001% to about 0.2% ketorolac in the oral cavity.

3 Claims, No Drawings

OTHER PUBLICATIONS

Lasfargues, J.J & J.L. Saffar,"Effect of Indomethacin on Bone Destruction During Experimental Periodontal Disease in the Hamster," Journal of Periodontal Research, vol. 18, pp. 110–117(1983).

Mroszcsak, E.J., F.W. Lee, D. Combs, F.H. Sarnquist, B–L Huang, A.T. Wu, L.G. Tokes, M.L. Maddox & D.K. Cho, "Keterolac Tromethamine Absorption, Distribution, Metabolism, Excretion, and Pharmacokinetics in Animals and Humans", Drug Metabolism & Disposition, vol. 15, No. 5, (1987), p. 618–626.

Nichols, F.C., D.A. Weber, R.L. Baker, B.R. Rifkin & A. Durakovic, "Bone Imaging of Experimentally Induced Periodontal Disease: Effects of Indomethacin," J. Dent. Res. vol. 58, Spec. Issue A, p. 415, Abstract No. 1298,(Jan. 1979).

Nuki, K., W.A. Soskolne, L.G. Raisz, K. S. Kornman & C. Alander, "Bone Resorbing Activity of Gingiva from Beagle Dogs Following Metronidazole and Indomethacin Therapy," Jornal of Periodontal Research, vol. 16. No. 2, pp. 205–212(Mar. 1981).

Nyman, S., H.E. Schroder & J. Lindhe, "Suppression of Inflammation and Bone Resorption by Indomethacin During Experimental Periodontitis in Dogs," J. Periodont., vol. 50, No. 9, pp. 450–461(Sep. 1979).

Offenbacher, S., L. D. Braswell, A.S. Loos, H.G. Johnson, C.M. Hall, H. McClure, J.L. Orkin, E.A. Strobert, M.D. Green & B.M. Odle, "The Effects of Flurbiprofen on the Progression of Periodontitis in Macca Mulatta," Journal of Periodontal Research, vol. 22, pp. 473–481 (1987).

Offenbacher, S., R.C. Williams, M. Jeffcoat, H. Howell, C.S. Mayambala, C.M. Hall & H.G. Johnson, "NSAIDs Effect on Periodontitis Sugests Central Role of PGEs and Thromboxane A₂," Journal of Dental Research, vol. 68, Spec. Issue, p. 240, Abstract #474, (Mar. 1989).

Reiff, R.L., C.L. White, D.N. Deines and T. Elattar, "Buffered Aspirin Oral Rinse in Reduction of Gingival Inflammation," J. Dent. Res., vol. 65, Spec. Issue, p. 788, Abstract#562 (Jun. 1986).

Rieger, M.M., "Topical Anti–inflammatory Therapy Against Periodontal Disease: A Historical Survey,"Clinical Preventive Dentistry, vol. 9, No. 4, pp. 18–22 (1987).

Rooks, W.H., P.J. Mahoney, L.D. Schott, M.E. Schuler, H. Sevelius, A.M. Strosberg, L. Tanenbaum, A.J. Tomolonis, M.B. Wallach, D. Waterbury & J.P. Yee,"The Analgesic and Anti–inflammatory Profile of Ketorolac and its Tromethamine Salt", Drugs Experimental Clinical Research, vol. XI, No. 8(1985), pp. 479–492.

Stalker, D.J. & S.R. Pollock, "Bioavailability of Flurbiprofen following Buccal Administration," Pharmaceutical Research, vol.8, No. 5, pp. 605–607, (1991).

"Vascular Endothelium Receptors and Transduction Mechanisms," NATO Series A: Life Sciences, vol. 175, p. 107(J.D. Catravas, C.N. Gillis & U.S. Ryan, Eds., Jul. 1989).

Vogel, R.I., "The Experimental Use of Anti–Inflammatory Drugs in the Treatment of Periodontal Diseases", Journal of Periodontology, vol. 56(suppl.)(1985), pp. 88–92.

Vogel, R.I., L.Schneider & D. Goteiner, "The Effects of a Topically–Active Non–Steroidal Anti–Inflammatory Drug on Ligature–Induced Periodontal Disease in the Squirrel Monkey", Journal of Clinical Periodontology, vol. 13(1986), pp. 139–114.

Vogel, R.I., S. A. Cooper, L.G. Schneider & D. Goteiner, "The Effects of Topical Steroidal and Systemic Nonsteroidal Anti–Inflammatory Drugs on Experimental Gingivitis in Man", Journal of Periodontology, vol. 55, No. 4 91984), pp. 247–251.

Waite, I.M., C.A. Saxton, A. Young, B. J. Wagg & M. Corbett, "The Periodontal Status of Subjects Receiving Non–Steroidal Anti–Inflammatory Drugs," Journal of Periodontal Research, vol. 16, No. 1 (Jan. 1981), p. 100–108.

Williams, R.C., "Non–Steroidal Anti–Inflammatory Drugs in Periodontal Disease," Non–Steroidal Anti–Inflamatory Drugs, A.J. Lewis, D.E. Furst, eds., Marcel Dekker, pub., (1987), pp. 143–55.

Williams, R., M.Jeffcoat, H. Howell, M. Reddy, C.Hall, H. Johnson & P. Goldhaber, "Naproxen Treatment of Periodontitis in Beagles", Journal of Dental Research, p. 243, Abstract No. 491, (Mar. 1989).

Williams, R.C., M.K. Jeffcoat, T.H. Howell, M. Reddy, C. M. Hall, H.G. Johnson, W.J. Wechter. & P/. Goldhaber, "Indomethacin or Flurbiprofen Treatment of Periodontitis in Beagles: Comparison of Effect on Bone Loss", Journal of Periodontal Research, vol.22(1987), pp. 403–407.

Williams, R.C., M.K. Jeffcoat, T.H. Howell, M.S. Reddy, H.G. Johnson, C.M. Hall & P. Goldhaber, "Topical Flurbiprofen Treatment of Periodontitis in Beagles", Journal of Periodontal Research, vol. 23, pp. 166–169 (1988).

Williams, R.C., M.K. Jeffcoat, T.H. Howell, M.S. Reddy, H.G. Johnson, C.M. Hall & P. Goldhaber, "Ibuprofen: An Inhibitor of Alveolar Bone Loss in Beagles", Journal of Periodontal Research, vol. 23, (1988), pp. 225–229.

Williams, R.C., M.K. Jeffcoat, T.H. Howell, A. Rolla, D.Stubbs, K.W. teoh, M.S. Reddy & P. Goldhaber, "Altering the Progression of Human Alveolar Bone Loss with the Non–Steroidal Anti–Inflammatory Drug Flurbiprofen", Journal of Periodontology, vol. 60 (1989), pp. 485–490.

Williams, R.C., M.K. Jeffcoat, W.J. Wechter, H.G. Johnson, M.L. Kaplan & P. Goldhaber, "Non–Steroidal Anti–Inflamatory Drug Treatment of Periondotitis in Beagles."Journal of Periodontal Research, vol., 19, pp. 633–637 (1984).

U.S. application No. 08/511,493, Kelm et al., filed Jul. 18, 1995.

U.S. application No. 08/270,163, Kelm et al., filed Jul. 25, 1994.

USE OF KETOROLAC FOR TREATMENT OF ORAL DISEASES AND CONDITIONS

This a division of application Ser. No. 08/280,163, filed on Jul. 25, 1994, now U.S. Pat. No. 3,464,609, which is a Continuation of Ser. No. 132,426, Oct. 5, 1993, abandoned, which is a continuation of Ser. No. 947,193, Sep. 18, 1992, abandoned, which is a continuation-in-part of Ser. No. 930,493, Aug. 14, 1992, abandoned, which is a continuation of Ser. No. 651,061, Feb. 8, 1991, abandoned, which is a continuation-in-part of Ser. No. 494,697, Mar. 16, 1990, abandoned.

TECHNICAL FIELD

The present invention relates to methods and compositions for the treatment of periodontal disease.

BACKGROUND OF THE INVENTION

"Periodontal disease", as used herein, is a broad term used to describe those diseases which attack the gingiva and the underlying alveolar bone supporting the teeth. Periodontal disease includes a series of diseases exhibiting various syndromes which vary from each other according to the stage or situation of the disease or the age of the patient, and have not been definitely subclassified. The term is used for any inflammatory disease which initially occurs at a marginal gingiva area and may affect the alveolar bone. Two common periodontal diseases are gingivitis (inflammation of the gingiva) and periodontitis (manifested by progressive resorption of alveolar bone, increasing mobility of the teeth, and loss of the teeth at advanced stage). Other terms used for various aspects of periodontal disease include "juvenile periodontitis", "acute necrotizing ulcertive gingivitis", and "alveolar pyorrhea". Periodontal disease is characterized by one or more of the following: inflammation of the gingiva, formation of periodontal pockets, bleeding and/or pus discharge from the periodontal pockets, resorption of alveolar bone, loose teeth and loss of teeth.

Periodontal disease is generally considered to be caused by/associated with bacteria which are generally present in dental plaque which forms on the surface of the teeth and in the periodontal pocket. Known methods for treating periodontal disease often include the use of antimicrobials.

Alveolar bone resorption is a loss of osseous tissue from the specialized bony structure which supports the teeth. Such resorption has many causes including, but not limited to, natural remodeling following tooth extraction, osseous surgery, periodontal flap surgery, dental implants, scaling and root planing and the progression of periodontal disease.

Certain nonsteroidal anti-inflammatory drugs (NSAIDs) have been shown to be useful in the treatment of periodontal disease, as disclosed in the following references: European Patent Application No. 0,137,668 of the Upjohn Company, inventor Wechter, published Apr. 17, 1985; Waite, I. M., C. A. Saxton, A. Young, B. J. Wagg & M. Corbett, "The Periodontal Status of Subjects Receiving Non-Steroidal Anti-Inflammatory Drugs", *Journal of Periodontal Research*, Vol. 16 (1981), pp. 100–108; Feldman, R. S., B. Szeto, H. J. Chauncey & P. Goldhaber, "Non-Steroidal Anti-Inflammatory Drugs in the Reduction of Human Alveolar Bone Loss", *Journal of Clinical Periodontology*, Vol. 10, No. 2 (1983), pp. 131–136; Vogel, R. I., S. A. Copper, L. G. Schneider & D. Goteiner, "The Effects of Topical Steroidal and Systemic Nonsteroidal Anti-Inflammatory Drugs on Experimental Gingivitis in Man", *Journal of Periodontology*, Vol. 55, No. 4 (1984), pp. 247–251; Vogel, R. I., "The Experimental Use of Anti-Inflammatory Drugs in the Treatment of Periodontal Disease:, *Journal of Periodontology*, Vol 56 (suppl) (1985), pp. 88–92; Vogel, R. I., L. Schneider & D. Goteiner, "The Effects of a Topically-Active Non-Steroidal Anti-Inflammatory Drug on Ligature-Induced Periodontal Disease in the Squirrel Monkey", *Journal of Clinical Periodontology*, Vol. 13 (1986), pp. 139–144; Williams, R. C., "Non-Steroidal Anti-Inflammatory Drugs in Periodontal Disease", *Non-Steroidal Anti-Inflammatory Drugs*, A. J. Lewis, D. E. Furst, eds., Marcel Dekker, pub., (1987), pp. 143–155; Williams, R. C., M. K. Jeffcoat, T. H. Howell, C. M. Hall, H. G. Johnson, W. J. Wechter & P. Goldhaber, "Indomethacin or Flurbiprofen Treatment of Periodontitis in Beagles: Comparison of Effect on Bone Loss", *Journal of Periodontal Research*, Vol. 22 (1987), pp. 403–407; Rieger, M. M., "Topical Antiinflammatory Therapy Against Periodontal Disease: A Historical Survey", *Clinical Preventive Dentistry*, Vol. 9, No. 4 (1987), pp. 18–22; Williams, R. C., M. K. Jeffcoat, T. H. Howell, M. S. Reddy, H. G. Johnson, C. M. Hall & P. Goldhaber, "Topical Flurbiprofen Treatment of Periodontitis in Beagles", *Journal of Periodontal Research*, Vol. 23 (1988), pp. 166–169; Jeffcoat, M. K., R. C. Williams, M. S. Reddy, R. English & P. Goldhaber, "Flurbiprofen Treatment of Human Periodontitis: Effect on Alveolar Bone Height and Metabolism", *Journal of Periodontal Research*, Vol. 23 (1988), pp. 381–385; Williams, R. C., M. K. Jeffcoat, T. H. Howell, M. S. Reddy, H. G. Johnson, C. M. Hall & P. Goldhaber, "Ibuprofen: An Inhibitor of Alveolar Bone Loss in Beagles", *Journal of Periodontal Research*, Vol. 23 (1988), pp. 225–229; Heasman, P. A., R. A. Seymour & P. F. Boston, "The Effect of a Topical Non-Steroidal Anti-Inflammatory Drug on the Development of Experimental Gingivitis in Man", *Journal of Clinical Periodontology*, Vol. 16 (1989), pp. 353–358; Williams, R., M. Jeffcoat, H. Howell, M. Reddy, C. Hall, H. Johnson & P. Goldhaber, "Naproxen Treatment of Periodontitis in Beagles", *Journal of Dental Research*, (1989), p. 243 (Abstract No. 491); Gaffar, A., J. Afflitto, E. J. Coleman, L. Steinberg & D. Fine, "Efficacy of Ibuprofen Rinse in a Subgingival Irrigator on Periodontitis in Primates", *Journal of Dental Research*, Vol. 68 (Special Issue) (1989), Abstract No. 830; and Williams, R. C., M. K. Jeffcoat, T. H. Howell, A. Rolla, D. Stubbs, K. W. Teoh, M. S. Reddy & P. Goldhaber, "Altering the Progression of Human Alveolar Bone Loss with the Non-Steroidal Anti-Inflammatory Drug Flurbiprofen," *Journal of Periodontology*, Vol. 60 (1989), pp. 485–490.

Ketorolac and its pharmaceutically-acceptable, non-toxic esters and salts are known NSAIDs. Ketorolac and its esters and salts, particularly its tromethamine salt, are disclosed in the following references: U.S. Pat. No. 4,089,969 issued to Muchowski & Kluge on May 16, 1978; Rooks, W. H., P. J. Maloney, L. D. Shott, M. E. Schuler, H. Sevelius, A. N. Strosberg, L. Tanenbaum, A. J. Tomolonis, M. B. Wallich, D. Waterbury & J. P. Yee, "The Analgesic and Anti-Inflammatory Profile of Ketorolac and its Tromethamine Salt", *Drugs Experimental Clinical Research*, Vol. XI, No. 8 (1985), pp. 479–492; and Mroszcsak, E. J., F. W. Lee, D. Combs, F. H. Sarnquist, B-L Huang, A. T. Wu, L. G. Tokes, M. L. Maddox & D. K. Cho, "Ketorolac Tromethamine Absorption, Distribution, Metabolism, Excretion, and Pharmacokinetics in Animals and Humans", *Drug Metabolism and Disposition*, Vol. 15, No. 5 (1987), pp. 618–626.

Several NSAIDs (e.g., ibuprofen and naproxen) are known to have more than one enantiomeric form which differ in properties from one another. Advantages of certain enantiomeric forms of NSAIDs are disclosed in the following references: PCT Patent Application No. WO/00421 of Sunshine & Laska, published Jan. 26, 1989; Caldwell, J., A. J. Hutt & S. Fournel-Gigleux, "The Metabolic Chiral Inversion and Disposition Enantioselectivity of the 2-Arylpropionic Acids and Their Biological Consequences", *Biochemical Pharmacology*, Vol. 37 (1988), pp. 105–114; and Hutt, A. J. & J. Caldwell, "The Metabolic Chiral Inversion of 2-Aryl-propionic Acids—A Novel Route with Pharmacologic Consequences", *Journal of Pharmacy and Pharmacology*, Vol. 35 (1983), pp. 693–704.

It is an object of the present invention to provide a topical, oral treatment for periodontal disease using ketorolac.

It is also an object of the subject invention to provide a topical, oral treatment for alveolar bone resorption using ketorolac.

It is a further object of the present invention to provide such treatments which result in minimal systemic (blood) concentration of ketorolac.

SUMMARY OF THE INVENTION

The present invention relates to methods and compositions for prevention or treatment of bone loss due to periodontal disease, oral osseous surgery, periodontal flap surgery, tooth extraction, dental implants, or scaling and root planing comprising topical administration, to mucosal tissues of the oral cavity, of a composition having from about 0.001% to about 0.2% ketorolac in the oral cavity.

DETAILED DESCRIPTION OF THE INVENTION

"Ketorolac", as used herein, is (±)-5-benzoyl-2,3-dihydro-1H-pyrrolizine-1-carboxylic acid, and the pharmaceutically-acceptable non-toxic esters and salts thereof, as disclosed in U.S. Pat. No. 4,089,96 issued to Muchowski & Kluge on May 16, 1978 which is incorporated by reference herein. The (−) or S enantiomer of ketorolac is preferred.

Pharmaceutically-acceptable esters of ketorolac include, but are not limited to, alkyl esters derived from hydrocarbons of branched or straight chain having one to about 12 carbon atoms. Examples of such esters are methyl, ethyl, propyl, isopropyl, butyl, t-butyl, isoamyl, pentyl, isopentyl, hexyl, octyl, nonyl, isodecyl, 6-methyldecyl and dodecyl esters.

Pharmaceutically-acceptable salts of ketorolac include salts derived from either inorganic or organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, and lithium salts. Salts derived from pharmaceutically-acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylene-diamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

A suitable salt of ketorolac is soluble in the composition of the subject invention in which it is incorporated. The preferred ketorolac salt for use in the compositions and methods of the present invention is ketorolac tromethamine, especially its (−) or S enantiomer, (−)5-benzoyl-2,3-dihydro-1H-pyrrolizine-1-carboxylic acid, 2-amino-2-(hydroxymethyl)-1,3-propanediol:

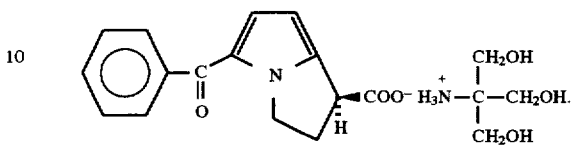

One aspect of the present invention is compositions comprising a safe and effective amount, preferably from about 0.001% to about 5%, more preferably from about 0.005% to about 1%, more preferably still from about 0.01% to about 0.5%, still more preferably from about 0.05% to about 0.2% ketorolac, and a pharmaceutically-acceptable topical, oral carrier. Also preferred are compositions comprising less than about 0.15% ketorolac, those comprising less than about 0.1% ketorolac and those comprising less than about 0.025% ketorolac. When mouthwashes and dental solutions having the above concentrations of ketorolac are used in the oral cavity, the effective concentrations of ketorolac solutions which contact the mucosal surfaces are essentially the same as given above, because dilution of the mouthwash or dental solution with saliva is minimal.

On the other hand, it is well known that dentifrices, when used in the mouth, are mixed with substantial amounts of saliva; the dilution amount is about 3:1 saliva to dentifrice (See U.S. Pat. No. 4,358,437, issued Nov. 9, 1982 to Duke, and U.S. Pat. No. 3,956,480 issued May 11, 1976 to Dichter et al., both incorporated herein by reference. The effective concentration of ketorolac solution in the mouth in contact with oral mucosa when a dentifrice is used, is about one-fourth the concentration of ketorolac in the dentifrice. Therefore, preferred concentrations of ketorolac in a dentifrice are about four times the above preferred mouthwash concentrations: from about 0.004% to about 20% to administer from about 0.001% to about 5% ketorolac. More preferable is a concentration of from about 0.02% to about 4%, more preferable still is from about 0.04% to about 2%, still more preferable is from about 0.2% to about 0.8% ketorolac to administer from about 0.005% to about 1%, from about 0.01% to about 0.5%, and from about 0.05% to about 0.2% ketorolac, respectively. Also preferred are dentifrice compositions comprising less than about 0.6% ketorolac, those comprising less than about 0.4% ketorolac, those comprising less than about 0.15%, and those comprising less than about 0.1% ketorolac to administer less than about 0.15%, less than about 0.1%, less than about 0.0375% and less than about 0.025% ketorolac, respectively.

The pH of the compositions of the present invention for which pH can be measured is preferably from about 2 to about 9, more preferably from about 4 to about 7, more preferably still from about 5 to about 6.

"Safe and effective amount", as used herein, means an amount of a substance high enough to provide a significant positive modification of the condition to be treated, but low enough to avoid serious side effects (at a reasonable benefit/risk ratio), within the scope of sound medical judgement. A safe and effective amount of the substance will vary with the particular condition being treated, the severity of the condition, the duration of the treatment, the nature of concurrent therapy, and like factors.

"Treat" and "treatment", as used herein, mean to attempt to slow the progress of or to reverse the symptoms of the condition being addressed.

"Effective" and "efficacy", as used herein, mean successful treatment of an adverse condition resulting in slowed or halted progression of alveolar bone resorption or reversal of such resorption.

"Topical, oral carrier", as used herein, denotes a carrier for the ketorolac which results in a composition which is administered topically to the oral cavity, held therein for a period of time, and then is largely expectorated rather than being swallowed. Such compositions include toothpastes, tooth gels, tooth powders, mouthwashes, mouthsprays, prophylaxis pastes, dental treatment solutions, and the like.

"Topical application", as used herein, means applied so as to contact exposed surfaces of the oral cavity with a composition or compound administered to the exposed surfaces of the oral cavity, preferably by swishing around in the mouth or brushing onto the teeth and/or over gum surfaces, preferably not administered so as to inject or specifically insert into interior cavities, e.g., periodontal pockets, within the oral cavity. The composition or compound is then preferably largely expectorated.

Components of the topical, oral carrier are suitable for administration to the oral cavity of a human or lower animal and are compatible with one another and the other components, especially the ketorolac, used in an oral composition of the present invention. The term "compatible" as used herein, means that the components of the compositions are capable of being commingled with one another, in a manner such that there is no interaction which would substantially reduce the efficacy of the oral composition under ordinary use conditions. Preferred topical, oral carriers thus provide the desired characteristics for toothpastes, tooth gels, tooth powders, mouthwashes, mouthsprays, prophylaxis pastes, dental treatment solutions, and the like. The topical, oral carriers of the present invention comprise components typically used in such compositions which are well known to a skilled practitioner. Such components include, but are not limited to anticaries agents, antiplaque agents, anticalculus agents, dental abrasives, surfactants, flavoring agents, sweetening agents, binders, humectants, thickening agents, buffering agents, preservatives, coloring agents and pigments, ethanol and water.

Water is an optional component of the topical, oral carriers of the compositions of the present invention. Water employed in the preparation of the commercially suitable compositions should preferably be of low ion content and free of organic impurities. Water preferably comprises from about 2% to about 99%, more preferably from about 20% to about 95% of the compositions of the present invention. When in the form of toothpastes, the compositions preferably are from about 2% to about 45%, more preferably from about 30% to about 40%, water, while mouthwashes are preferably from about 45% to about 95%, more preferably from about 75% to about 90%, water.

Dental abrasives useful in the topical, oral carriers of the compositions of the present invention include many different materials. The material selected must be one which is compatible within the composition of interest and does not excessively abrade dentin. Suitable abrasives include, for example, silicas including gels and precipitates, insoluble sodium polymetaphosphate, hydrated alumina, and resinous abrasive materials.

A class of preferred abrasives for use in the subject compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehydes, melamine-urea-formaldehydes, cross-linked epoxides, and cross-linked polyesters.

Silica dental abrasives are also preferred in the compositions of the present invention. The silica abrasive polishing material generally has an average particle size ranging between about 0.1 and about 30 microns, preferably between 5 and 15 microns. The abrasive can be precipitated silica or silica gels such as the silica xerogels described in U.S. Pat. No. 3,538,230 issued to Pader & Wiesner on Mar. 2, 1970, and in U.S. Pat. No. 3,862,307 issued to DiGuilio on Jan. 21, 1975. Preferred are the silica xerogels marketed under the tradename Syloid® by the W. R. Grace & Co., Davison Chemical Division. Preferred precipitated silica materials are those marketed by the J.M. Huber Corporation under the tradename Zeodent®, particularly the silica carrying the designation Zeodent 119®. These silica abrasives are described in U.S. Pat. No. 4,340,583 issued to Wason on Jul. 29, 1982.

Mixtures of abrasives can be used. All of the above patents regarding dental abrasives are incorporated herein by reference.

The total amount of abrasive in dentifrice compositions of the present invention preferably range from about 10% to about 70% by weight; toothpastes preferably contain from about 10% to about 50% by weight of abrasives. Solution, mouthspray and mouthwash compositions of the present invention may contain quantities of abrasive as low as 0%.

Flavoring agents are preferred in the topical, oral carriers of the compositions of the present invention in order to make them more palatable. Typical flavoring agents include menthol, oil of wintergreen, oil of peppermint, oil of spearmint, oil of sassafras, and oil of clove. If present, flavoring agents are generally included in the subject compositions in amounts of from about 0.04% to about 2% by weight.

Sweetening agents are also preferred in the topical, oral carriers of the compositions of the present invention in order to make them more palatable. Typical sweetening agents include saccharin salts, dextrose, levulose, thaumatin, aspartame, D-tryptophan, dihydrochalcones, acesulfame and cyclamate salts, especially sodium cyclamate and sodium saccharin. If present, sweetening agents are generally included in the subject compositions in amounts of from about 0.01% to about 5% by weight.

Another optional component of the topical, oral carriers of the compositions of the present invention is a humectant. The humectant serves to keep toothpaste compositions from hardening upon exposure to air, and to give mouthwash and toothpaste compositions a moist feel to the mouth. Certain humectants can also impart desirable sweetness of flavor to mouthwash and toothpaste compositions. The humectant, on a pure humectant basis, generally comprises from about 0% to about 70%, preferably from about 2% to about 55%, by weight of the compositions herein. Suitable humectants for use in compositions of the present invention include edible polyhydric alcohols such as glycerin, sorbitol, xylitol, polyethylene glycol, and propylene glycol, especially sorbitol and glycerin.

Buffering agents are another optional component of the topical, oral carrier of the compositions of the present invention. The buffering agents serve to retain the pH of the compositions within the preferred range. The buffering agent generally comprises from about 0% to about 10%, preferably from about 0.2% to about 5%, by weight of the compositions herein. Suitable buffering agents for use in compositions of the present invention include soluble phosphate salts.

Other optional components of the topical, oral carriers of the compositions of the present invention are preservatives. The preservatives prevent microbial growth in the compositions. Suitable preservatives include methylparaben, propylparaben, benzoates and ethanol. If the preservative is ethanol, it generally comprises from 0% to about 35%, preferably from about 5% to about 15%, of the compositions herein. Other preservatives generally comprise from about 0% to about 5%, preferably from about 0.1% to about 2%, by weight of the compositions herein.

Binders and thickening agents may be used in the topical, oral carriers of the compositions of the present invention, particularly in toothpaste compositions. Preferred binders and thickening agents include, for example, carrageenan (e.g., Irish moss, Viscarin TP-5 which is an iota carrageenan), cellulose derivatives (e.g., hydroxyethyl cellulose, sodium carboxymethyl cellulose, sodium carboxymethyl hydroxypropyl cellulose), carboxyvinyl polymers (carbomers), natural gums (e.g., gum karaya, gum arabic, gum tragacanth), polysaccharide gums (e.g., xanthan gum), fumed silica, and colloidal magnesium aluminum silicate. If present, these binders and thickening agents are generally present in the compositions of the present invention in amounts of from about 0.1% to about 5%.

Compositions of the present invention may also contain a surfactant. Suitable surfactants are those which are reasonably stable and preferably form suds through the pH range of the compositions. Surfactants useful as sudsing agents may be soaps, and anionic, nonionic, cationic, zwitterionic and amphoteric organic synthetic detergents, and compatible mixtures thereof. Surfactants of these types are described more fully in U.S. Pat. No. 3,959,458 issued to Agricola, Briner, Granger & Widder on May 25, 1976, incorporated herein by reference. Such surfactants are generally present in the compositions of the present invention at a level of from about 0% to about 10%, preferably from about 0.2% to about 5%. Surfactants may also be used as solubilizing agents to help retain sparingly soluble components, e.g., some flavoring agents, in solutions. Surfactants suitable for this purpose include polysorbates and poloxamers.

The compositions of the present invention may also comprise an anticaries agent. Preferred anticaries agents are water-soluble fluoride ion sources. Fluoride ions also generally help stabilize pyrophosphate (generally an anticalculus agent) in the oral cavity, thus enhancing the benefits provided by any soluble pyrophosphate included in the compositions. The number of such fluoride ion sources is great and includes those disclosed in U.S. Pat. No. 3,535,421 issued Oct. 20, 1970 to Briner & Widder, incorporated herein by reference. Preferred fluoride ion source materials include: sodium fluoride, potassium fluoride, and sodium monofluorophosphate and mixtures thereof. Sodium fluoride is the preferred fluoride source. The amount of the fluoride ion source in the oral compositions of the present invention, if present, is preferably sufficient to provide from about 0.005% to about 0.35%, more preferably from about 0.05% to about 0.3% of fluoride ions in the compositions.

Antimicrobial antiplaque agents can also optionally be present in the oral compositions of the present invention, on the condition that they are compatible with the ketorolac. Such agents may include Triclosan, 5-chloro-2-(2,4-dichlorophenoxy)phenol, as described in *The Merck Index*, 10th ed. (1976), p. 1381; U.S. Pat. No. 3,506,720; and European Patent Application No. 0,251,591 of Beecham Group, PLC, published Jan. 7, 1988, chlorhexidine, (*Merck Index*, No. 2090), alexidine (*Merck Index*, No. 222); hexetidine (*Merck Index*, No. 4624); sanguinarine (*Merck Index*, No. 8320); benzalkonium chloride (*Merck Index*, No. 1066); salicylanilide (*Merck Index*, No. 8299); domiphen bromide (*Merck Index*, No. 3411); cetylpyridinium chloride, (CPC) (*Merck Index*, No. 2024); tetradecylpyridinium chloride, (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and peroxides, such as cylium peroxide, hydrogen peroxide, and magnesium monoperthalate and its analogs as described in U.S. Pat. No. 4,670,252; and analogs and salts of the above antimicrobial antiplaque agents. If present, the antimicrobial antiplaque agents generally comprise from about 0.1% to about 5% by weight of the compositions of the present invention.

Nutrients can also be present in oral compositions of the present invention, on condition that they are compatible with the ketoralac Active. Such agents may include folate, retinoids (Vitamin A), Vitamin C, Vitamin E and zinc. If present, the nutrients generally comprise from about 0.001% to about 10% by weight of the compositions of the present invention.

Compositions of the present invention may also include one or more anticalculus agents, on the condition that they are compatible with the ketorolac. Anticalculus agents which may be useful in the compositions of the present invention include pyrophosphates or polyphosphates such as those disclosed in U.S. Pat. No. 4,590,066 issued to Parran & Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict & Sunberg on Apr. 28, 1987; polyepoxysuccinates such as those disclosed in U.S. Pat. No. 4,846,650 issued to Benedict, Bush & Sunberg on Jul. 11, 1989; ethylenediaminetetraacetic acid as disclosed in British Patent No. 490,384 dated Feb. 15, 1937; nitrilotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt-Dunker & Gloxhuber on Oct. 26, 1976 and U.S. Pat. No. 4,877,603 issued to Degenhardt & Kozikowski on Oct. 31, 1989; all of these patents are incorporated herein by reference. If present, the anticalculus agents generally comprise from about 0.2% to about 13%, preferably from about 0.4% to about 6% of the compositions of the present invention.

Preferred compositions of the present invention are in the form of toothpastes. Components of such toothpastes generally include a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpastes may also include one or more of an anticaries agent (from about 0.05% to about 0.3% as fluoride ion), an anti-calculus agent (from about 0.1% to about 13%), and an antiplaque agent (from about 0.1% to about 5%).

Other preferred compositions of the present invention are mouthwashes and mouthsprays. Components of such mouthwashes and mouthsprays include water (from about 45% to about 95%), ethanol (from about 0% to about 25%), a humectant (from about 0% to about 50%), a surfactant agent (from about 0.01% to about 7%), an flavoring agent (from about 0.04% to about 2%), a sweetening agent (from about 0.1% to about 3%), and a coloring agent (from about 0.001% to about 0.5%). Such mouthwashes and mouthsprays may also include one or more of an anticaries agent (from about 0.05% to about 0.3% as fluoride ion), an anticalculus agent (from about 0.1% to about 3%), and an antiplaque agent (from about 0.1% to about 5%).

Other preferred compositions of the present invention are dental solutions. Components of such dental solutions generally include water (from about 90% to about 99%), preservative (from about 0.01% to about 0.5%, thickening agent (from about 0% to about 5%), flavoring agent (from about 0.04% to about 2%), sweetening agent (from about 0.1% to about 3%), and surfactant (from 0% to about 5%).

Another aspect of the present invention involves methods of preventing or treating periodontal disease by topical application of compositions comprising a safe and effective amount of ketorolac, to the mucosal tissues of the oral cavity, especially the gingival mucosa. Such compositions are described hereinabove. Preferred are methods for treating periodontal disease by topical application, to gingival mucosa afflicted with the disease, of a safe and effective amount of ketorolac.

Methods of treating or preventing bone resorption due to oral osseous surgery, tooth extraction, dental implants, or scaling and root planing may also be accomplished through topical application of the compositions of the present invention described hereinabove. Preferred methods for treating or preventing such resorption is by topical application of a safe and effective amount of such compositions to the gingival mucosa surrounding the bone area to be treated.

The subject invention relates to a method for prevention or treatment of bone loss due to periodontal disease, oral osseous surgery, periodontal flap surgery, tooth extraction, dental implants, or scaling and root planing, comprising topical administration to gingival mucosal tissues of the oral cavity of a composition having a safe and effective amount of ketorolac in the oral cavity. Such compositions in the oral cavity preferably comprise from about 0.001% to about 5%, more preferably from about 0.001% to about 1%, more preferably from about 0.001% to about 0.2%, more preferably from about 0.01% to about 0.15%, also preferably from about 0.05% to about 0.1%, also preferably less than 0.025% ketorolac.

It has unexpectedly been found that, whereas the use of other nonsteroidal anti-inflammatory drugs for the topical treatment of periodontal disease in the oral cavity has resulted in substantial systemic concentrations of the drug, the systemic concentration of ketorolac resulting from the methods of the present invention is very low, as long as swallowing of the composition is substantially avoided. While the systemic concentration of ketorolac resulting from its topical application is very low, a substantial amount of the ketorolac is found in the crevicular fluid, which flows from the gingival tissues.

In contrast to the low systemic and high crevicular fluid concentrations of ketorolac which result from the topical administration methods of the present invention, peroral dosage of NSAIDs has been reported to result in high systemic concentration of the dosed NSAID and a low concentration of the NSAID in the gingival crevicular fluid. This unexpected benefit resulting from topical application of ketorolac compositions is highly desirable, because it avoids the adverse side effects of high systemic concentration of NSAID. It is well known that possible adverse effects from the peroral use and/or high systemic concentrations of NSAIDs include nausea, indigestion, diarrhea and peptic ulcer, as well as more severe toxic side effects (see, The American Medical Association Encyclopedia of Medicine, 730 (C. Klayman, Ed., 1989); see also, D. R. Robinson, *Osteoarthritis*, Medicine 15:X (Scientific American, September 1991)).

The treatment of periodontal disease by the topical application of ketorolac not only reduces inflammation caused by the disease, but also unexpectedly reduces the rate of alveolar bone resorption (bone loss) characteristic of periodontitis. Topically administered ketorolac not only reduces alveolar bone loss, but also unexpectedly causes an increase in bone height and in bone density. Additionally the increase in bone occurs in both horizontal and vertical bony defects, whereas previous treatments which provide bone increases, e.g., scaling and root planing, and periodontal flap surgery, have exhibited the ability to cause bone increases only in vertical bony defects. Horizontal increase in bone dimension does not appear to have been achieved previously through any known treatment.

Dental procedures such as osseous surgery, tooth extraction, periodontal flap surgery, dental implantation, and scaling and root planing are typically the cause of some alveolar bone resorption, perhaps followed by partial bone repair. Treatment with compositions of the present invention not only prevents the initial bone resorption, but aids in the repair of bone and possibly increases the amount of bone repaired. Consequently, recovery following these various dental procedures is hastened, and better oral health is achieved than with other available treatments.

The methods of the present invention preferably involve the contact of a composition of the present invention with oral cavity tissue afflicted with periodontal disease, or following osseous surgery, tooth extraction, periodontal flap surgery, dental implantation, or scaling or root planing, for at least about 15 seconds, preferably from about 20 seconds to about 10 minutes, more preferably from about 30 seconds to about 60 seconds. Typically, this is achieved by conventional methods of tooth brushing, rinsing the mouth with mouthwash or dental solution, etc. The composition is placed in the mouth, swished around or brushed on the teeth and outer gum surfaces and largely expectorated. The compositions preferably are not actively inserted into the periodontal pocket; in such cases, any introduction of the compositions into such pockets occurs from essentially passive contact at the surface opening of the pocket.

The following examples are provided as illustrations of the composition and methods of the present invention, but are not limitations of the scope of the present invention.

EXAMPLES 1 AND 2

Examples of toothpaste compositions of the present invention are as follows:

| Ingredients | Example 1 (Wt. %) | Example 2 (Wt. %) |
|---|---|---|
| Sorbitol | 42.00 | 35.00 |
| Saccharin Sodium | 0.13 | 0.20 |
| FD&C Blue (1% soln) | 0.05 | 0.05 |
| Precipitated Silica | 20.00 | 25.00 |
| Sodium Fluoride | — | 0.24 |
| Flavor | 0.90 | 1.50 |
| Purified Water | qs | qs |
| Sodium Alkyl Sulfate | 1.00 | 1.20 |
| Phosphoric Acid | 0.40 | — |
| Carbomer 940 | 0.25 | 0.25 |
| Xanthan Gum | 0.50 | 0.65 |
| Titanium Dioxide | 0.50 | 0.50 |
| Ketorolac Tromethamine | 0.05 | 0.10 |

EXAMPLES 3 AND 4

Examples of mouthwash compositions of the present invention are as follows:

| Ingredients | Example 3 (Wt. %) | Example 4 (Wt. %) |
|---|---|---|
| Ketorolac Tromethamine | 0.10 | 0.01 |
| Ethanol | 12.00 | 15.00 |
| Glycerin | 10.00 | 12.00 |
| Dibasic Sodium Phosphate Heptahydrate | 0.07 | 0.48 |
| Saccharin Sodium | 0.08 | 0.08 |
| Monobasic Sodium Phosphate Monohydrate | 2.03 | 1.82 |
| Polysorbate 80 | 0.33 | 0.33 |
| FD&C Blue (1% Soln) | 0.02 | 0.02 |
| Flavor | 0.15 | 0.15 |
| Purified Water | qs | qs |

EXAMPLE 5

An example of a dental solution of the present invention is as follows:

| Ingredients | Example 5 (Wt. %) |
|---|---|
| Water | qs |
| Ketorolac Tromethamine | 0.15 |
| Flavor | 0.10 |
| Polysorbate 80 | 0.25 |
| Saccharin Sodium | 0.05 |
| Methylparaben | 0.20 |
| Propylparaben | 0.10 |

EXAMPLES 6 AND 7

Examples of toothpaste compositions of the present invention are as follows:

| Ingredients | Example 6 (Wt. %) | Example 7 (Wt. %) |
|---|---|---|
| Sorbitol | 37.20 | 37.20 |
| Glycerine | 19.00 | 19.00 |
| Polyethylene Glycol 600 | 3.00 | 3.00 |
| Sodium Saccharin | 0.17 | 0.17 |
| Precipitated Silica | 20.00 | 20.00 |
| Sodium Fluoride | 0.24 | 0.24 |
| Flavor | 0.90 | 0.90 |
| Purified Water | qs | qs |
| Sodium Alkyl Sulfate | 1.00 | 1.00 |
| Monobasic Sodium Phosphate, Monohydrate | 5.00 | 5.00 |
| Fumed Silica | 2.00 | 2.00 |
| Carboxymethylcellulose | 0.30 | 0.30 |
| Titanium Dioxide | 0.50 | 0.50 |
| Ketorolac Tromethamine | 0.15 | 1.00 |

While particular embodiments of the present invention have been described, it will be obvious to those skilled in the art that various changes and modifications to the present invention can be made without departing from the spirit and scope of the invention. It is intended to cover, in the appended claims, all such modifications that are within the scope of this invention.

What is claimed is:

1. A method for prevention or treatment of bone loss due to periodontal flap surgery comprising topical administration to gingival mucosal tissue of the oral cavity after surgery, of a composition providing from about 0.001% to about 0.2% of ketorolac in the oral cavity, wherein said composition is not swallowed and is expectorated after about at least 15 seconds in the mouth.

2. The method of claim 1 wherein the composition providing such ketorolac levels is flavored dental solution.

3. The method of claim 2 wherein the ketorolac consists substantially of the (−) of S enantiomer.

* * * * *